US008568657B2

(12) United States Patent
Braet et al.

(10) Patent No.: US 8,568,657 B2
(45) Date of Patent: Oct. 29, 2013

(54) BIOREACTOR PROBE CONNECTION SYSTEM

(75) Inventors: Christophe Braet, Sint-Katelijne-Waver (BE); Tom Claes, Bilzen (BE); Steven Vanhamel, Velm (BE); Nicolas Havelange, Brussels (BE)

(73) Assignee: ATMI BVBA, Hoegaarden (BE)

( * ) Notice: Subject to any disclaimer, the term of this patent is extended or adjusted under 35 U.S.C. 154(b) by 654 days.

(21) Appl. No.: 12/664,398

(22) PCT Filed: Jun. 11, 2008

(86) PCT No.: PCT/US2008/066577
§ 371 (c)(1),
(2), (4) Date: May 24, 2010

(87) PCT Pub. No.: WO2008/157181
PCT Pub. Date: Dec. 24, 2008

(65) Prior Publication Data
US 2010/0255526 A1 Oct. 7, 2010

Related U.S. Application Data

(60) Provisional application No. 60/944,490, filed on Jun. 16, 2007.

(51) Int. Cl.
*A61L 2/00* (2006.01)
*A61L 2/18* (2006.01)
*A61L 9/00* (2006.01)
A61L 2/08 (2006.01)
B01J 19/00 (2006.01)

(52) U.S. Cl.
USPC ............... 422/28; 422/26; 422/27; 422/40; 422/291; 422/292; 422/294

(58) Field of Classification Search
USPC ................ 422/292, 294, 26, 27, 28, 40, 291
See application file for complete search history.

(56) References Cited

U.S. PATENT DOCUMENTS 3,830,106 A * 8/1974 Gardiner et al. ........... 73/863.23
3,997,447 A * 12/1976 Breton et al. .............. 210/360.2
4,695,551 A 9/1987 Samhaber et al.
(Continued)

OTHER PUBLICATIONS

Pall Corporation, Kleenpak™ Sterile Connectors product information, Web document downloaded from http://www.pall.com/main/Biopharmaceuticals/Product.page?id=34125, retrieved Aug. 27, 2012.

*Primary Examiner* — Regina M Yoo
(74) *Attorney, Agent, or Firm* — Vincent K. Gustafson; Jenkins, Wilson, Taylor & Hunt, P.A.

(57) ABSTRACT

A system providing a sterile connection between a sensor probe and a fluid processing apparatus (e.g., a bioreactor) includes a first probe receiving element mountable to the fluid processing apparatus and a second probe receiving element having a gas-permeable contaminant barrier material and coupleable to the first probe receiving element. A sensor probe may be mounted to the second probe receiving element, with the combination being sterilized with a sterilant gas such as steam. Following such sterilization, connection between the first and second probe receiving elements is made through matable sterile couplings, and the probe is insertable through the coupled receiving elements to a position in fluid contact with the interior of the fluid processing apparatus.

18 Claims, 13 Drawing Sheets

(56) References Cited

U.S. PATENT DOCUMENTS

| | | |
|---|---|---|
| 5,891,100 A | 4/1999 | Fleckenstein |
| 6,003,362 A | 12/1999 | Dieckmann et al. |
| 6,655,655 B1 | 12/2003 | Matkovich |
| 7,160,590 B2 | 1/2007 | Vanhamel et al. |
| 7,249,880 B2 | 7/2007 | Zambaux |
| 7,384,783 B2 * | 6/2008 | Kunas et al. ............... 435/289.1 |
| 7,431,494 B2 | 10/2008 | Zambaux |
| 7,434,372 B2 | 10/2008 | Vanhamel et al. |
| 7,901,934 B2 * | 3/2011 | Kunas et al. ............... 435/289.1 |
| 2003/0082070 A1 * | 5/2003 | Liberto et al. ............... 422/1 |
| 2005/0239198 A1 * | 10/2005 | Kunas et al. ............... 435/297.1 |
| 2005/0239199 A1 | 10/2005 | Kunas et al. |
| 2006/0270036 A1 | 11/2006 | Goodwin et al. |
| 2008/0206847 A1 * | 8/2008 | Kunas et al. ............... 435/287.1 |
| 2009/0323466 A1 | 12/2009 | Vanhamel et al. |
| 2010/0015696 A1 | 1/2010 | Claes et al. |

* cited by examiner

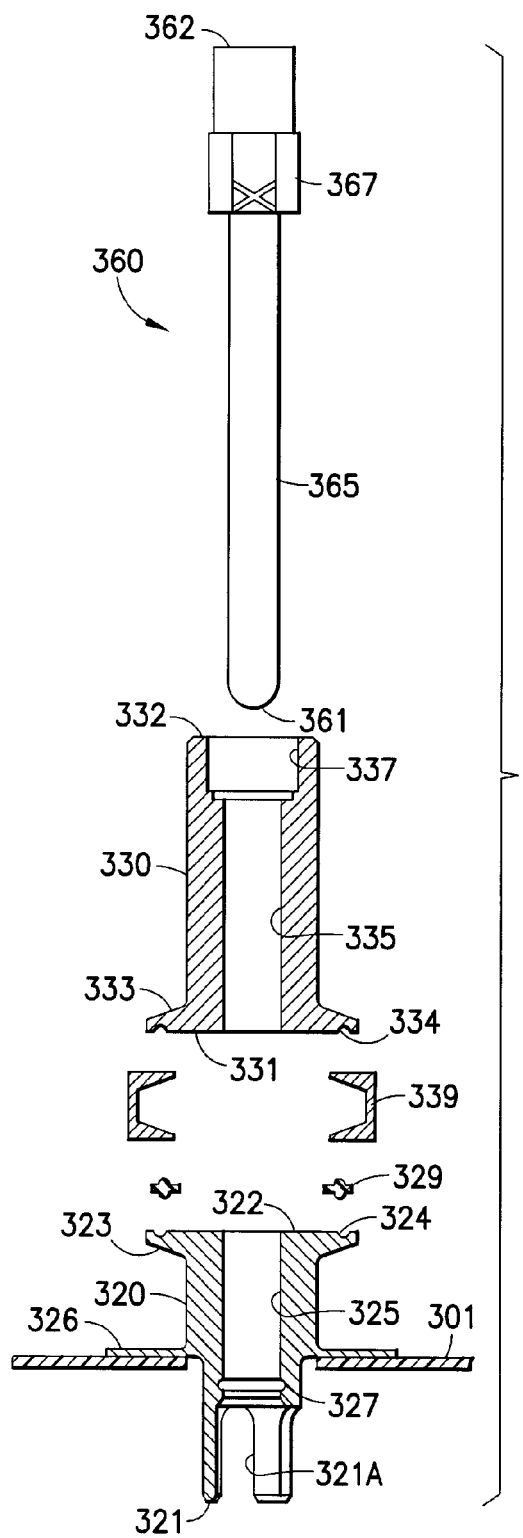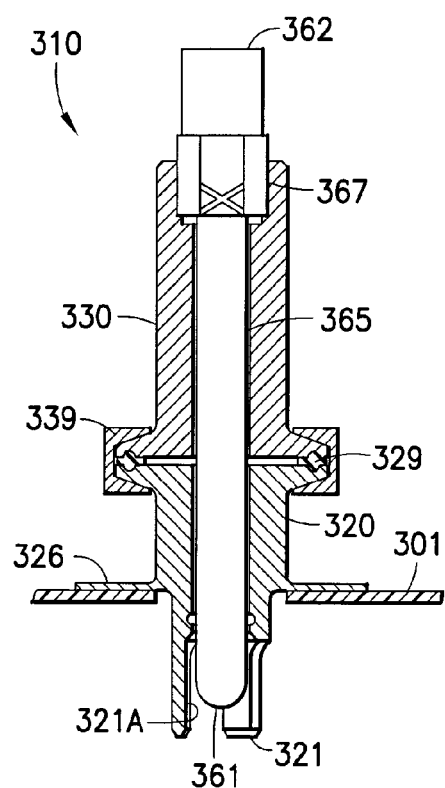
FIG.3A
FIG.3B

BIOREACTOR PROBE CONNECTION SYSTEM

STATEMENT OF RELATED APPLICATION

This application is a U.S. national phase under the provisions of 35 U.S.C. §371 of International Application No. PCT/US08/66577 filed on Jun. 11, 2008, which in turn claims priority of U.S. Provisional Patent Application No. 60/944,490 filed on Jun. 16, 2007. The disclosures of such international application and U.S. priority application are hereby incorporated by reference herein in their respective entireties, for all purposes.

FIELD OF THE INVENTION

This invention generally relates to bioreactors and similar fluid processing systems, and more specifically to systems and methods for connecting probe-type sensors to such systems.

DESCRIPTION OF THE RELATED ART

A bioreactor may be defined as a mechanical vessel in which organisms are cultivated in a controlled manner, and/or materials are converted via specific reactions. Bioreaction processes have wide industrial applicability, including biotechnological production of substances such as pharmaceuticals, antibodies, or vaccines, and bioconversion of organic waste.

Although quite similar to conventional chemical reactors, bioreactors differ in that they are specifically designed to influence metabolic pathways. Traditional chemical reactor models and designs that may be used for bioreaction as well include: continuous stirred-tank reactors, continuous flow stirred-tank reactors, plug-flow reactors, ebullized-bed (i.e., "bubbling and boiling") reactors, and fluidized-bed reactors. Although the term "bioreactor" is often used synonymously with "fermenter," in the strictest definition, a fermenter is a system that provides an anaerobic process for producing alcohol from sugar.

Bioreactors differ from conventional chemical reactors in that they support and control biological entities. As such, bioreactor systems must be designed to provide a higher degree of control over process upsets and contaminations, since the organisms are more sensitive and less stable than chemicals. Biological organisms, by their nature, will mutate, which may alter the biochemistry of the bioreaction or the physical properties of the organism. Analogous to heterogeneous catalysis, deactivation or mortality occur and promoters or coenzymes influence the kinetics of the bioreaction. Although the majority of fundamental bioreactor engineering and design issues are similar, maintaining the desired biological activity and eliminating or minimizing undesired activities often presents a greater challenge than traditional chemical reactors typically require.

The goal of an effective bioreactor is to control, contain and positively influence the biological reaction. An area of major importance in bioreactor design is control of bioreaction parameters, including: temperature; pH, oxygen availability, water availability, nutrient availability, and product and byproduct removal. In addition to controlling these, a bioreactor must be designed to both promote formation of the optimal morphology of the organism and to eliminate or reduce mutation of the desired organism or contamination by unwanted organisms.

Perhaps the most common type of aerobic bioreactor in current use is the stirred-tank reactor. Traditional bioreactors include stainless steel tanks having components for introducing air into the contents of the tank. Such components may include a various openings (e.g., as in a perforated pipe) disposed along the bottom of the tank. Mixing with an agitator is preferably performed fairly gently, so as to avoid damage to cellular material.

Due to multiple advantages (such as elimination of inter-batch carryover or contamination, and elimination of inter-batch cleaning and/or sterilization operations) disposable containers are becoming increasingly useful in many industrial applications, including stirred-tank mixing applications. For example, a mixing apparatus employing a disposable and flexible mixing tank liner having a mixing paddle adapted to travel within the liner is disclosed in U.S. Patent Application Publication No. 2005/0078552, assigned to Advanced Technology Materials, Inc. (Danbury, Conn.) and incorporated by reference herein. Additionally, disposable bioreactor systems employing thin-film materials have recently become available from manufacturers such as Hyclone (Logan, Utah, USA), Wave Biotech (Somerset, N.J., USA), and Applikon Biotechnology (Schiedam, Netherlands).

One challenge associated with providing a disposable bioreactor vessel is providing reliable interfaces to various types of sensors, as may be useful to monitor temperature, carbon dioxide, pH, or other desirable parameters. If film-based liner materials are used in disposable bioreactor vessels, it may be difficult to make reliable fluidic or sensory connections while avoiding leakage and potential contamination, due to the non-rigid character of such liner materials.

Given potential variability in flow and thermal conditions along a wall of a bioreactor vessel, sensor probes that protrude through such a vessel wall into the interior of a bioreactor are traditionally used to provide more reliable measurements of the conditions experienced by the bioreactor contents. The presence within the vessel of a continuously moving mixing element (e.g., an agitator) in conjunction with an inwardly-protruding sensor probe, however, elevates the risk that a sensor probe may be damaged or broken in use. Given the extremely long periods of time inherent to certain bioprocessing operations (for example, such as on the order of a few days for fermentation, and up to 30 days or more for cell culture operations), the potential ruination of an entire batch of bioprocessed material by a damaged sensor may be burdensome and/or costly to remedy.

A further difficulty relates to maintaining sterile conditions within a bioreactor when one or more insertable probes are used. Probes and disposable bioreactor liners may be provided by different vendors, and due to the high cost of most probes, they are generally sterilized and re-used between batches. Yet the very process of inserting a probe into a pre-sterilized (e.g., disposable liner-based) bioreactor inherently involves exposure of the probe—and concomitant risk of contamination—if the insertion step is performed outside of a cleanroom environment. It would be desirable to permit reliably sterile insertion of a probe into a bioreactor without requiring such step to be performed in a cleanroom environment.

Thus, there exists a need for improved bioreactor systems to address one or more of the above-identified difficulties. Desirable systems would include disposable elements to avoid or minimize the need for cleaning and sterilization between batches.

SUMMARY OF THE INVENTION

This present invention relates in various aspects to systems and methods permitting sterile connection between a probe and fluid processing apparatus, such as a bioreactor.

In a first separate aspect, the invention relates to a system adapted for sterile connection of a probe with a fluid processing apparatus having an interior, the system comprising: (I) a first probe receiving element having (a) a mounting element adapted to engage a portion of said probe; (b) a gas-permeable contaminant barrier material adapted to admit a sterilant gas or vapor into an interior volume of said first probe receiving element, said interior volume including a first passage permitting insertion of at least a portion of said probe therethrough; and (c) a first coupling; and (II) a second probe receiving element securable to said fluid processing apparatus, the second probe receiving element defining a second passage and having a second coupling matably engageable to the first coupling, wherein following engagement between the first coupling and the second coupling, the system is adapted to receive at least a portion of said probe through the second passage to a position in fluid communication with the interior of said fluid processing apparatus.

In a second separate aspect, the invention relates to a probe receiving element adapted to permit sterile connection of a probe with a fluid processing apparatus having an interior and an associated first coupling element adapted to permit the insertion of at least a portion of a probe therethrough, the probe receiving element comprising: (i) a mounting element adapted to engage a portion of said probe; (ii) a contaminant barrier material adapted to admit a sterilant gas or vapor into an interior volume of said probe receiving element, said interior volume including a passage permitting insertion of at least a portion of said probe; and (iii) a second coupling matably engageable to the first coupling; wherein following engagement between the first coupling and the second coupling, the system is adapted to receive at least a portion of said probe through the engaged coupling elements to a position in fluid communication with the interior of said fluid processing apparatus.

In another separate aspect, the invention relates to a method to permit sterile connection of a probe with a fluid processing apparatus having an interior, the method comprising: (I) inserting an elongated probe into a first probe receiving element having (a) a mounting element adapted to engage a portion of said probe; (b) a gas-permeable contaminant barrier material bounding an interior volume including a first passage permitting insertion of at least a portion of said probe therethrough; and (c) a first coupling; (II) following said probe insertion, supplying a sterilant gas or vapor through the gas-permeable contaminant barrier material into an interior volume of said first probe receiving element to sterilize said probe; (III) matably engaging the first probe receiving element to a second probe receiving element securable to said fluid processing apparatus, the second probe receiving element defining a second passage, wherein said engagement is between a second coupling of said second probe receiving element and the first coupling; and (IV) inserting a portion of the probe through the engaged first and second coupling to a position in fluid communication with the interior of said fluid processing apparatus.

In another aspect, any of the foregoing aspects may be combined for additional advantage.

Other aspects, features and embodiments of the invention will be more fully apparent from the ensuing disclosure and appended claims.

BRIEF DESCRIPTION OF THE DRAWINGS

FIG. 3A is a side cross-sectional assembly view of a sensor probe assembly adjacent to a portion of a wall of a fluid processing vessel.

FIG. 3B is an assembled cross-sectional view of the sensor probe assembly and fluid processing vessel wall portion of FIG. 3A.

DETAILED DESCRIPTION OF THE INVENTION, AND PREFERRED EMBODIMENTS THEREOF

Various embodiments of the present invention are directed to systems and methods permitting sterile connection of a probe with a fluid processing apparatus, such as a bioreactor. To provide context for such embodiments, various fluid processing apparatuses will first be discussed.

In one embodiment, preferred fluid processing vessels or tanks comprise flexible liner materials, such as to permit the tank to conform to the inner surface of an external support container and then be disposed after a single use (e.g., to eliminate inter-batch carryover or contamination, and eliminate inter-batch cleaning and/or sterilization operations). A fluid processing tank may be manufactured from pyrogen free, sterile materials, to reduce risks associated with cross contamination. The flexible fluid processing tank may comprise one or more ports for filling, spiking, aerating, adding and/or draining components to reduce the amount of human contact with the various components (which may be hazardous, dangerous and/or infectious) that are to be mixed as part of and during the mixing of such components. If a flexible mixing tank such as one fabricated with a polymeric film is employed, then it is preferably used in conjunction with a substantially rigid external supporting container to provide support for the flexible tank. As used herein, the term "film" refers to a thermoplastic film made using a film extrusion and/or foaming process, such as a cast film or blown film extrusion process. For the purposes of the present invention, the term includes nonporous films as well as microporous films. Films may be vapor permeable or vapor impermeable, and function as liquid barriers under normal use conditions.

Figure 1:
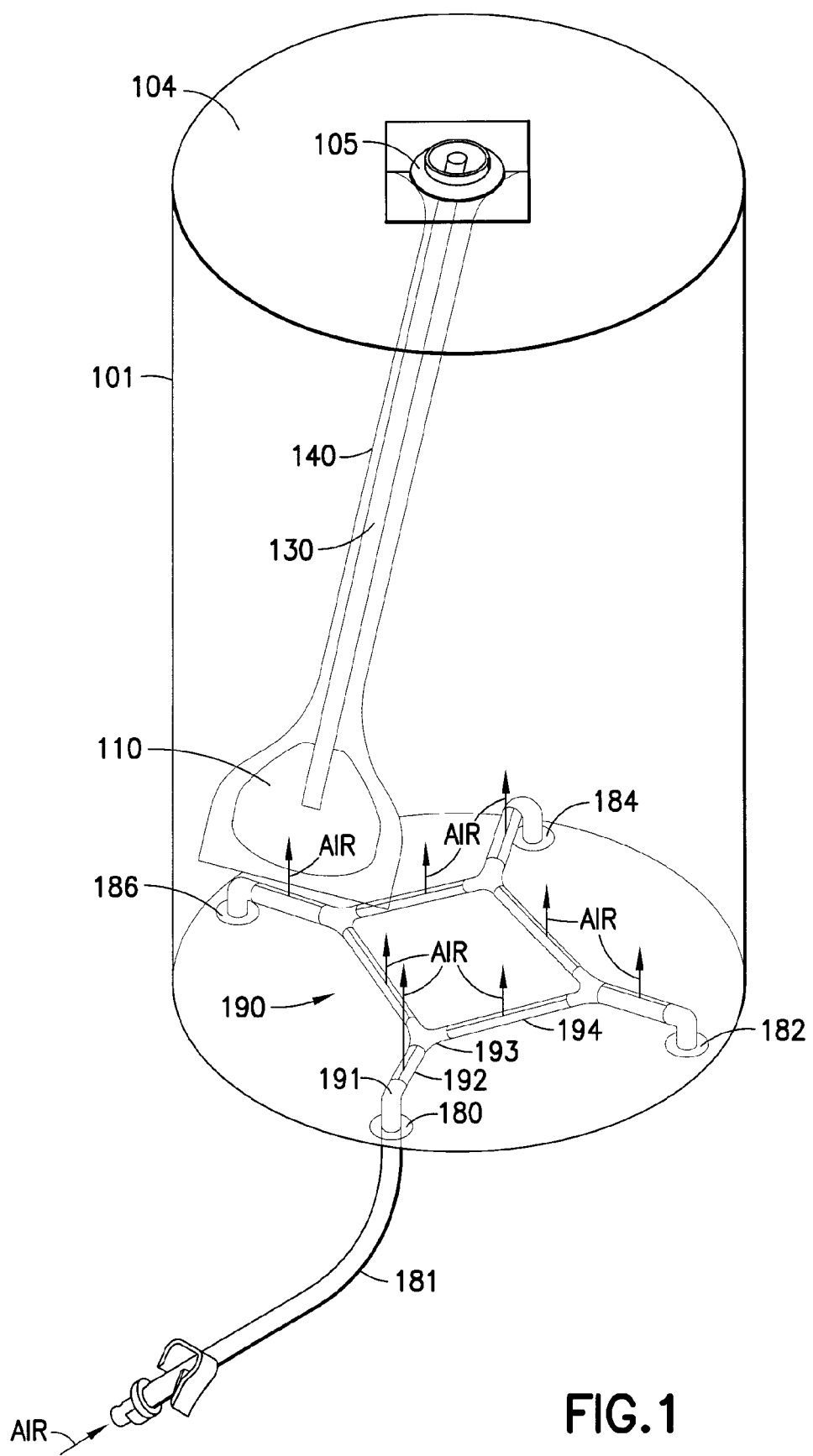
FIG. 1 illustrates a perspective view of a cylindrical fluid processing vessel useable as a bioreactor, the vessel including a mixing paddle disposed within an integral sleeve, and including an air distribution manifold including perforated tubes disposed along the bottom of the tank, with arrows indicating the direction of air passage into the interior of the vessel.

Referring to FIG. 1, a fluid processing tank 101 may include various components to render it suitable for use as a bioreactor apparatus 101. The tank 101 includes a moveable mixing paddle 101 disposed within an integral flexible sleeve 140 (preferably formed of a polymeric film and bonded to the top wall 104 of a liner-based tank 101.) The mixing tank and sleeve may be manufactured from any suitable material. In one embodiment, the mixing tank and sleeve are made of any suitable material having a property where upon removal of an extending force, it is capable of substantially recovering its original size and shape and/or exhibits a significant retractive force. As such, the mixing tank and sleeve may be made of any suitable type of stretchable, collapsible, pliable and/or elastic material. In a preferred embodiment, a disposable mixing tank is manufactured from a fully transparent film to allow for visual inspection of the tank's contents before and after use.

A motor (not shown) is preferably provided to drive the paddle via an intermediate support rod 130. The paddle is preferably adapted to travel within the tank 101 along a defined path without continuous rotation of the paddle 110 about a support rod 130 supporting the paddle 110. The sleeve 140 has an associated coupling guide 150 that permits pivotal movement of the paddle through a defined path within the tank 101, and the coupling guide 105 further mates with a top wall portion 104 of the tank 101. The paddle may be further adapted to travel within the tank through a defined path at a nonzero angle relative to the central axis, such as in a substantially conical path. Such paddle-based non-rotary mixing is gentler than the rotary (shear) mixing effected by a conventional impeller, particularly where large-diameter impellers are used (e.g., in large vessels) since the tip speed of an impeller can become quite high.

The tank 101 may include an internal air distribution manifold or sparger 190 in fluid communication with an external air or gas source (not shown) via an air or gas inlet 180. The sparger 190 may be assembled from elbow fittings 191, peripheral perforated tubes 192, Y-fittings 193, and central perforated tubes 194, which permit air to be injected along the bottom of the tank 101 in a dispersed manner as small bubbles without requiring the use of high speed turbine agitators (impellers). Microperforated or microporous tubes may be used in place of the tubes 192, 194. Anchors 182, 184, 186, not requiring external fluidic connections, may be provided to secure the sparger 190 to the tank 101. Alternatively, gas inlets 182, 184, 186 may be substituted for the anchors if desired to aid in gas distribution and/or permit multiple gases to be mixed in the sparger 190 and supplied to the tank 101. While not shown in FIG. 1, a tank 101 would desirably include one or more additional inlet and outlet connections of various types, such as to permit the addition or removal of various substances and/or enable sensors to be provided in sensory communication with the interior of the tank 101.

Figure 2:
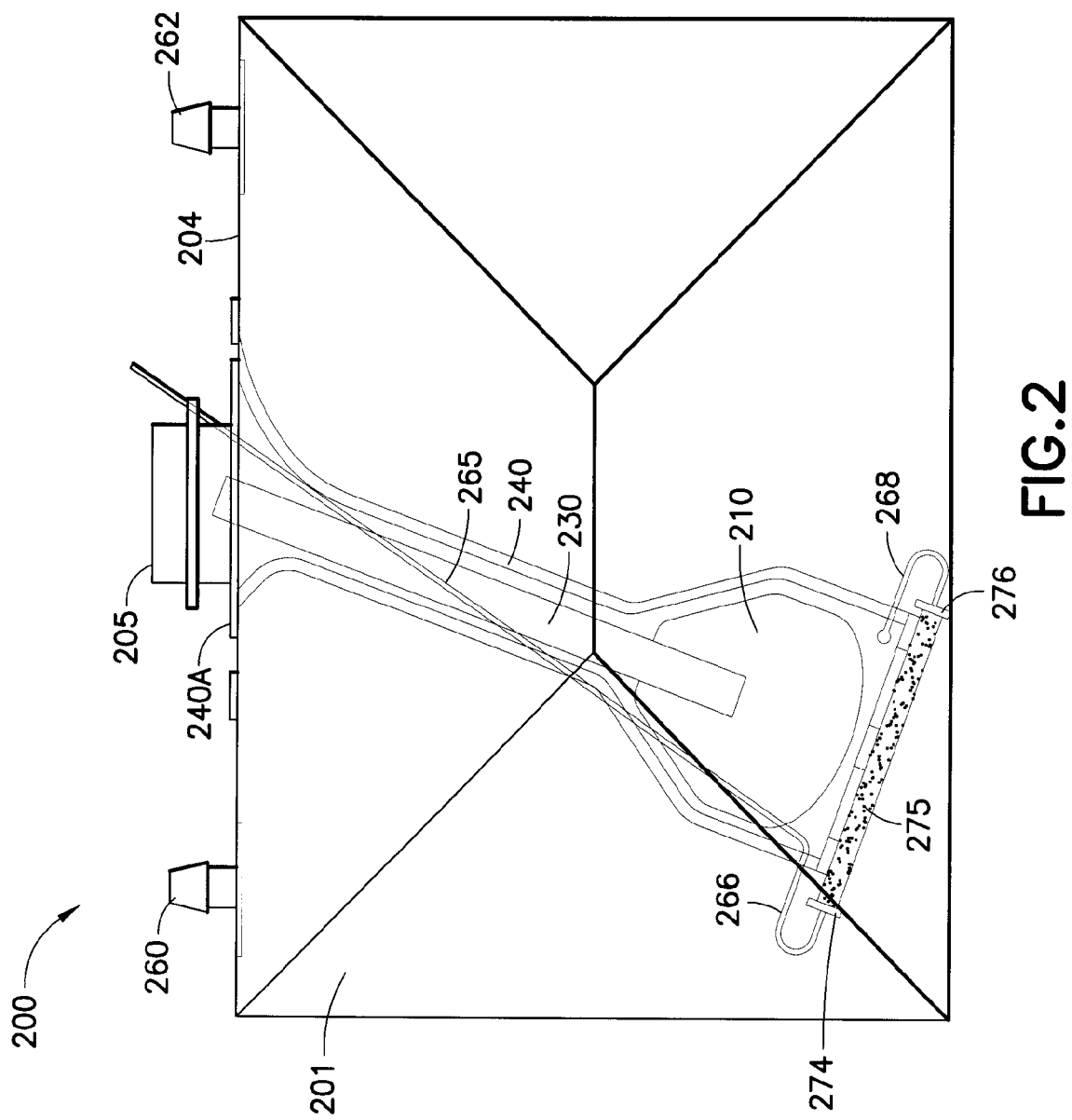
FIG. 2 illustrates a side view of a parallelepiped-shaped fluid processing vessel useable as a bioreactor, the vessel including a mixing paddle disposed within an integral sleeve, and including a paddle-mounted sparger for supplying oxygen to the interior of the vessel.

As the preceding cylindrical fluid processing tank 101 may not promote optimal conditions for certain bioreaction processes, a shorter parallelepiped-shaped fluid processing apparatus may be used. It is to be appreciated that tanks of any suitable shape may be employed in embodiments according to the present invention. Such an apparatus 200 is shown in FIG. 2, including a parallelepiped-shaped mixing vessel 201 having an integral sleeve 240 with a mixing paddle 210 disposed therein, and with a support rod 230 is linked to the paddle 210 within the sleeve 240. To provide enhanced mass transfer, a sparger 275 may be adapted to travel with a mixing paddle 210 and supply gas to the interior of the vessel 201. Near the paddle 210, the sparger 275 is provided outside the sleeve 240 to enable fluid communication with the contents of the tank 201. A gas supply conduit 265 in fluid communication with the sparger 275 may be disposed within the sleeve 240. As illustrated, the sparger 275 comprises a microporous or microperforated tubular material. End caps 274, 275 may be provided along the ends of the tubular material. A conduit segment 268 supports the sparger 275 outside the sleeve 240 and provides fluid communication with the gas supply conduit 265. A second conduit segment 266 may be provided along the other end of the sparger 275, but such segment 266 need not be in fluid communication with the sparger 275. Because the paddle 210 does not rotate continuously about a longitudinal axis of the support rod 230, there is no danger of twisting the gas supply conduit 265 to the point of failure. The tank 201 further includes a coupling guide 205 (that is preferably more rigid than a film material with which the tank is preferably constructed) that permits pivotal arrangement of the support rod 230 between an external kinetic energy source (not shown) and the interior of the tank 201. Ports 260, 262 may be provided along an upper surface of the tank 201.

To permit use of a fluid processing apparatus or tank as a bioreactor, various sensors may be provided in sensory communication with the contents of the tank. While certain parameters such as temperature might be performed through the wall of a mixing tank, such indirect measurement is not preferred due to the insulating effect of the tank wall and attenuated response, particularly in large-volume systems. As a result, providing one or more sensors in direct communication (contact) with the contents of the mixing tank is preferred. Direct sensory contact may be provided by inserting one or more sensor probes into the interior of a mixing tank. Alternatively, direct sensory contact may be provided with a recirculation loop that withdraws a portion of the tank contents through a sensing line and then returns the contents to the tank.

Figure 3C:
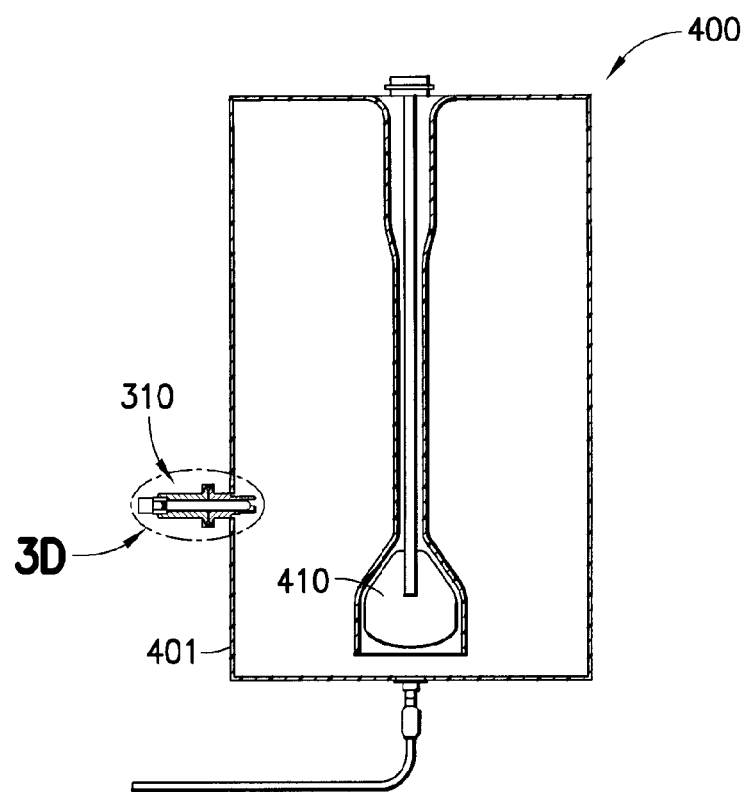
FIG. 3C is a simplified side cross-sectional view of a fluid processing vessel having an associated sensor probe assembly according to FIGS. 3A-3B disposed along a side wall of the vessel.
Figure 3D:
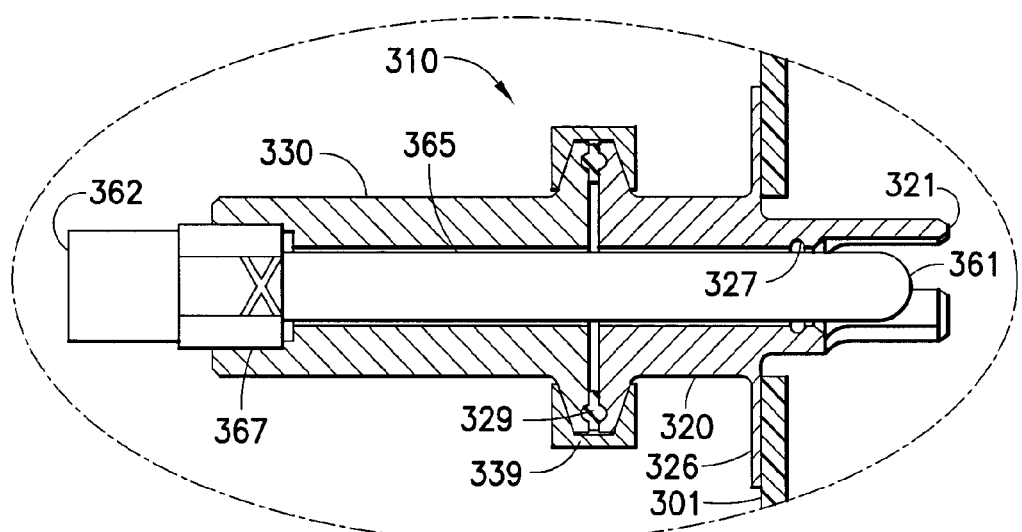
FIG. 3D is a magnified view of the sensor probe assembly and a portion of the fluid processing vessel of FIG. 3C.

While sensor probes are conventionally employed in rigid mixing tanks, it is more challenging to integrate probes with flexible (e.g., disposable) mixing tanks—such as tanks fabricated of polymeric film materials—due to the difficulties in providing adequate structural support between a probe and tank while maintaining a fluid-tight interface. A sensor probe assembly 310 suitable for insertion into a flexible mixing tank and adapted to overcome these difficulties is illustrated in FIGS. 3A-3D. A sensor probe 360 includes a shaft portion, proximal end 362, distal end 361 (for contacting contents of a mixing tank 600), and an increased diameter travel stop 367. A fluid processing tank 400 having a mixing paddle 410 and a flexible wall 401 is illustrated in FIG. 3C. Along the tank wall 401, a first neck 320 having a first internal bore 325 is sealed to the tank wall 601, preferably by welding (e.g., ultrasonic or solvent welding, for example) along a reinforcing flange 326). The first neck 320 includes a distal end 321 having a recess 321A adapted to permit fluid to circulate past the distal end 361 of the sensor probe 360 when the probe 360 is fully inserted into the first neck 320. The first neck 320 further includes a recess 327 adapted to receive an O-ring (not shown) to sealingly engage the probe shaft 365 to the first neck 320 along the bore 325. The proximal end 322 of the first neck 320 includes a first flared portion 323 defining a first recess 324 adapted to engage an O-ring 329. A second neck 330 having a proximal end 332 and a distal end 331 is adapted to mate with the first neck 320 along a second flared portion 333 defining a second recess 334 also adapted to engage the O-ring 329. An outer collar 339 is provided to mechanically join the first neck 320 and the second neck 330 along the flared portions 323, 333. The second neck 330 further defines an expanded bore portion 337 adapted to mate with the increased diameter travel stop portion 367 of the probe 360.

The sensor 360 may include any of various types of sensors, such as may be useful to monitor temperature, pressure, pH, oxygen concentration, chemical (e.g., $CO_2$ presence, chemical concentration, and other desirable parameters. Although only a single sensor assembly 310 is shown in FIG. 3C, it is to be appreciated that any desirable number of sensors may be inserted into or otherwise provided in fluid communication with a flexible mixing tank such as described hereinabove.

The sensor 360 may be used in conjunction with any suitable control components to provide an informational or feedback signal. For example, a parameter such as temperature of contents within the tank may be sensed with the sensor to generate an output signal, and that signal may be used in conjunction with heat exchange components (e.g., an external heater or chiller) to responsively control the temperature of contents within the tank.

Figure 4A:
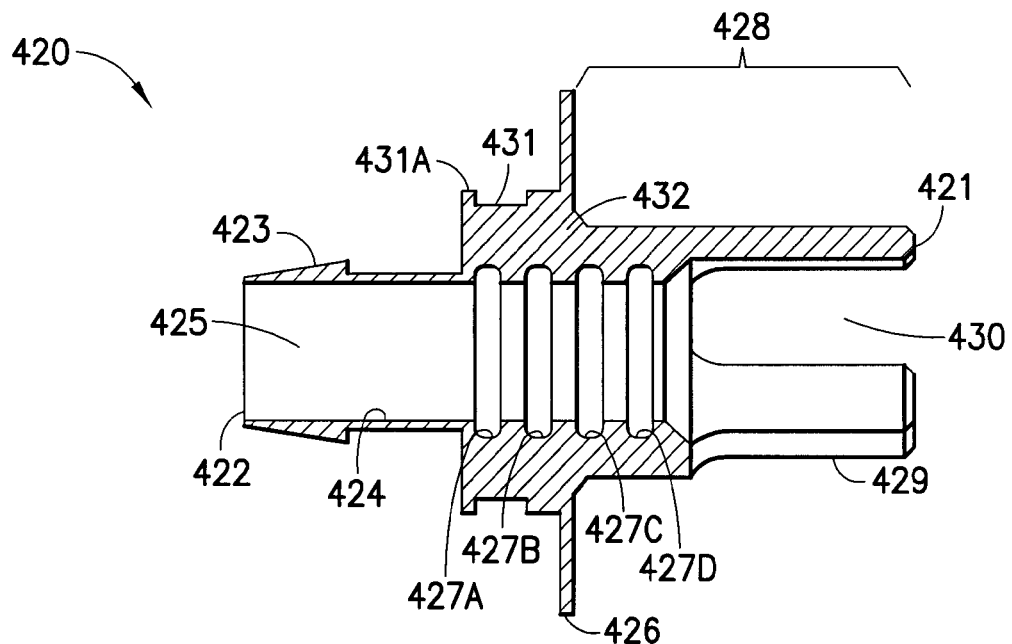
FIG. 4A is a side cross-sectional view of a fitment matable with a fluid processing vessel and adapted for use with a sensor probe, the fitment including a first protective surround permitting contents of the fluid processing apparatus to circulate across at least a portion of a probe, and further including four recesses adapted to retain O-rings or other sealing elements for sealing against a sensor probe insertable therethrough.

FIG. 4A is a side cross-sectional view of a fitment 420 matable with a fluid processing vessel and adapted for use with a sensor probe. The fitment 420 may be formed by any suitable manufacturing process, including injection molding, milling, and the like. Polymeric materials are contemplated for use in fabricating the fitment 420. The fitment 420 has a body 432 and includes a first end 421 and a second end 422 having an inner surface 424 defining a bore 425 therethrough. Along the first end, the fitment 420 includes a first protective surround 429 having an opening 430 permitting contents of an associated fluid processing apparatus (not shown) to circulate across at least a portion of a probe (not shown). In this manner, deleterious contact between a mixing element (e.g., paddle) and a potentially fragile probe may be avoided. Along the second end 422, the probe includes a flared or barb-type male fitting 423 for mating with a tube (not shown). The fitment 420 includes an outer surface 431 that may define a tube stop 431A. The fitment 420 further includes four recesses 427A-427D adapted to retain O-rings or other sealing elements (not shown) for sealing against a sensor probe insertable therethrough. The multiple sealing elements fittable into the recesses 427A-427D are preferably provided to guard against leakage, which can be particularly detrimental in bioreaction processes. To ensure that maximal volume is retained within the fluid processing vessel, the sealing elements are preferably disclosed adjacent to a tip portion of a sensor probe insertable into the fitment 420. The fitment 420 has a radially protruding flange 426 that may be welded directly to a film-based liner; alternatively, any suitable coupling method including adhesive bonding, may be used. So coupled, a contact portion 428 of the fitment 428 protrudes into an associated liner or vessel (not shown).

Figure 4B:
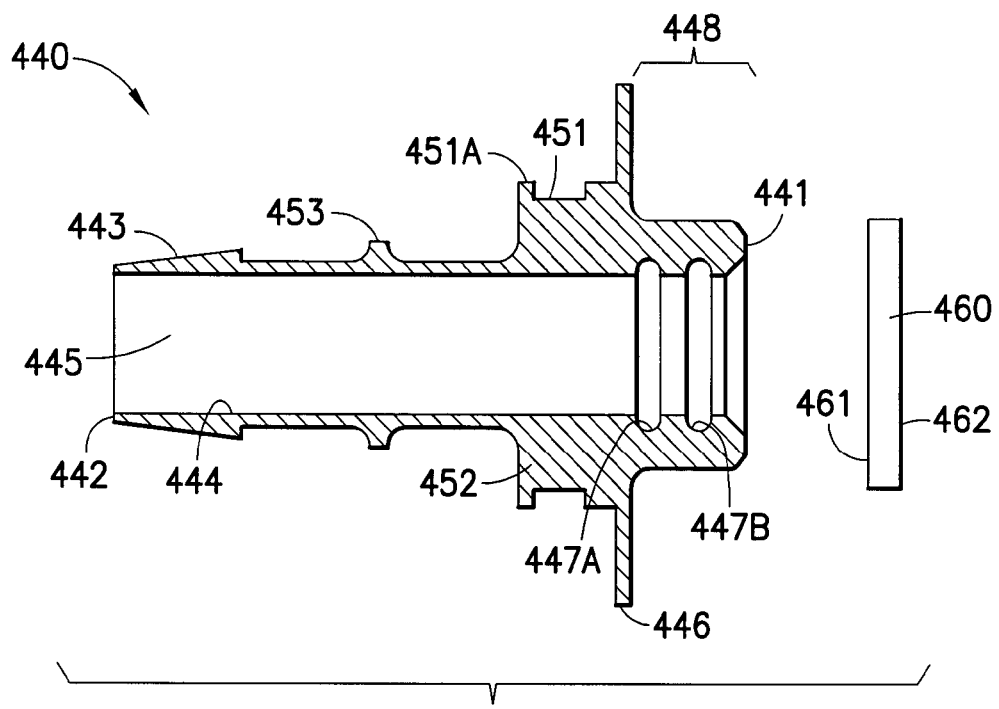
FIG. 4B is a side cross-sectional assembly view of another fitment matable with a fluid processing vessel and adapted for use with a sensor probe, with a removable or rupturable cap or membrane engageable to the fitment, the fitment further including two recesses adapted to retain O-rings or other sealing elements for sealing against a sensor probe insertable therethrough.

FIG. 4B is a side cross-sectional assembly view of another fitment 440 matable with a fluid processing vessel and adapted for use with a sensor probe, lacking a protective surround (such as the surround 429 illustrated in FIG. 4A) but including a removable or rupturable cap or membrane 460 engageable to the fitment 440. The fitment 440 has a body 452, a first end 441, and a second end 442. The first end 441 is intended for insertion into a liner, with the flange portion 446 being sealable to the liner, and with a contact portion 448 of the fitment 448 protruding into the liner. It is noted that the contact portion 448 of the instant fitment 440 is significantly smaller than the contact portion 428 illustrated in FIG. 4A. Continuing to refer to FIG. 4B, the second end 442 includes a flared or barb-type male fitting 443 adapted for mating with a tube (not shown). A further raised protrusion 453 and tube landing surface 451A may be defined along the exterior surface 451 of the fitment 440. The fitment 440 further includes two recesses 447A, 447B adapted to retain O-rings or other sealing elements (not shown) for sealing against a sensor probe insertable through the bore 445 of the fitment 440 bounded by an inner surface 444. In one embodiment, a rupturable membrane 462 adapted to rupture upon the insertion of a sensor probe is provided. Such a rupturable membrane may be scored or pre-cut to promote predictable rupture thereof. In another embodiment, a cap 462 (with inner surface 461 and outer surface 462) is adhered or otherwise bound to the fitment 440, and subsequently removed prior to usage of the probe.

Figure 5:
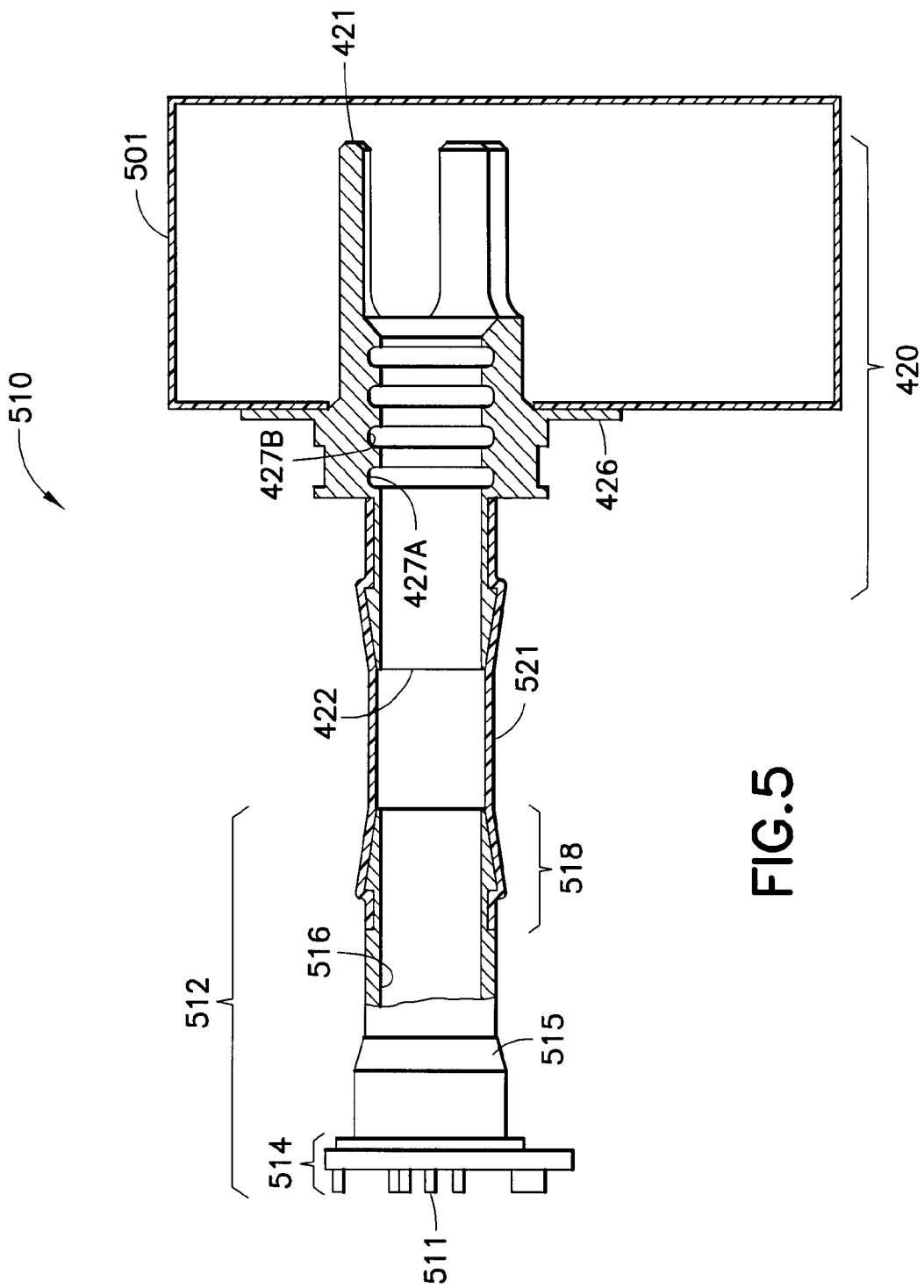
FIG. 5 is a side cross-sectional view of a vessel-mountable inner probe receiving element secured by a fitment (i.e., the fitment of FIG. 4A) along one end to a fluid processing vessel, the probe receiving element having a coupling, preferably adapted for sterile connection to another like coupling, along another end thereof.

FIG. 5 is a side cross-sectional view of a vessel-mountable inner probe receiving element 510 secured by a fitment 420 (i.e., the fitment of FIG. 4A) along one end 421 to a fluid processing vessel 501 (which is preferably includes a polymeric film-based liner). The term "inner" as used in the context of the inner probe receiving element 510 refers to proximity of a receiving element relative to the fluid processing vessel 501. The probe receiving element 510 includes a coupling 514, preferably adapted for sterile connection to another like coupling (e.g., the coupling 554 of FIGS. 6A-6B), along another end 511 thereof. Such matable couplings 514, 554 are preferably adapted for sterile connection to one another in a non-sterile environment. For example, Kleenpak® connectors (Pall Corp., East Hills, N.Y.) may be used. The coupling 514 preferably includes a tubular extension 515 having an inner wall 516 defining a bore for receiving a sensor probe, and a flared or barb-type male fitting 518 for receiving a tube 521 (e.g., platinum cured silicone tubing) that provides a passage between the fitment 420 and the coupling 514. The fitment 420 includes first end 421, second end 422, a flange portion 426 for mating with a fluid processing vessel 501, and multiple recesses (e.g., recesses 427A, 427B) for receiving sealing elements such as O-rings (not shown) for sealable engagement of a sensor probe (not shown) insertable into the probe receiving element 510.

Figure 6A:
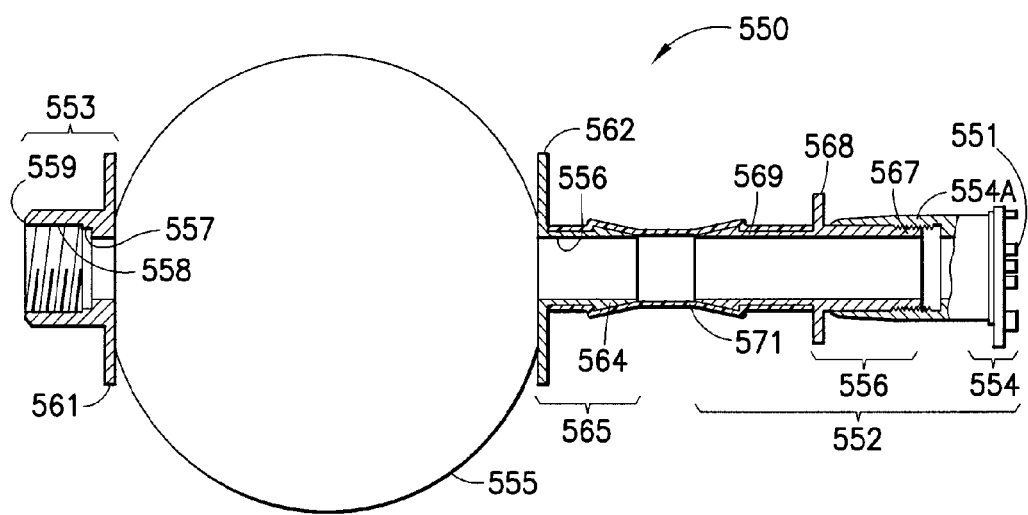
FIG. 6A is a side cross-sectional view of an outer probe receiving element adapted to mate with the vessel-mountable inner probe receiving element of FIG. 5, with the outer probe receiving element being in a first expanded state suitable for sterilizing a sensing probe inserted therein.

FIG. 6A is a side cross-sectional view of an outer probe receiving element 550 adapted to mate with the vessel-mountable inner probe receiving element 510 of FIG. 5, with the outer probe receiving element 550 being in a first expanded state suitable for sterilizing a sensing probe (not shown) inserted therein. The outer probe receiving element 550 has a first end 551 including a coupling 554 and a second end 559 including a probe mounting element 553 preferably including a threaded female fitting portion 558 and a sealing surface 557 adapted to engage a sealing portion of a sensor probe. The outer probe receiving element 550 includes a gas-permeable contaminant barrier material 555 (e.g., a spun-bonded olefin material) adapted to admit a sterilant gas or vapor into an interior portion (e.g. a volume bounded by inner surface 556 and by the barrier material 555) of said outer probe receiving element 550. The sterilant gas or vapor may include, for example, steam and/or ethylene oxide. Flange portions 561, 562 may be disposed on either side of the contaminant barrier material 555. One flange portion 562 may include a tubular extension 565 having a flared or barb-type male fitting 564 adapted to mate with a tube 571 (e.g., a platinum cured silicone tube). The tube 571 provides connection to a connector portion 569 of a coupling assembly 552 having a coupling 554 disposed along one end 551 thereof. The coupling assembly 552 may include a tube stop 568 bounding a tubular portion 566 having a threaded end 567 thereof for mating with a housing portion 554A of the coupling 554.

Upon insertion of a probe into the outer probe receiving element 550, the combination may be substantially sealed except through the gas-permeable contaminant barrier material 555, as the probe is preferably adapted to sealingly engage the mounting element 553 of the outer probe receiving element 550, and at the opposite end 551 of such outer probe receiving element 550, a coupling 554 preferably adapted for sterile connection to another like coupling (e.g., the coupling 511 of FIG. 5) is provided. Such coupling 554 of the outer probe receiving element 550 preferably remains substantially sealed until mated with a like coupling (e.g., coupling 514) and an interposing membrane or barrier of one or both couplings 554, 514 is removed. A primary benefit of such coupling type is that a sterile connection may be made in a non-sterile environment—i.e., outside of a cleanroom. The mated probe and outer probe receiving element 550 combination represents a sealed volume except for the gas-permeable contaminant barrier material 555. Such combination may be inserted into an autoclave and sterilized together, as steam passes through the gas-permeable contaminant barrier material. As an alternative to steam, any of various sterilant gases such as ethylene oxide may be used.

Figure 6B:
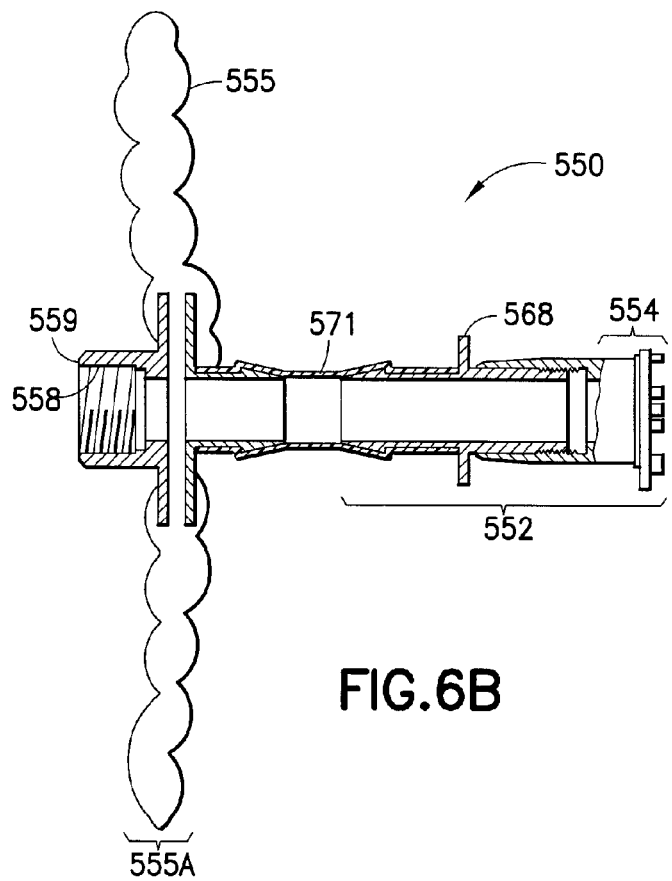
FIG. 6B is a side cross-sectional view of the outer probe receiving element of FIG. 6A, in a second compressed state suitable for delivering a sensing portion of a probe retained therein to a sensing position or area.

FIG. 6B is a side cross-sectional view of the outer probe receiving element 550 of FIG. 6A, in a second compressed state suitable for delivering a sensing portion of a probe retained therein to a sensing position or area. The outer probe receiving element 550 includes a collapsible section 555A (e.g., between flange portions 561, 562) comprising said contaminant barrier material 555, providing an adjustable length to the outer probe receiving element 550. The position shown in FIG. 6B is used to shorten the length of the outer probe receiving element 550, to insert a portion of the probe into and through the inner probe receiving element 510 (e.g., of FIG. 5) to a desired position in fluid communication with an interior portion of said fluid processing apparatus (e.g., apparatus 501 of FIG. 5).

Figure 7:
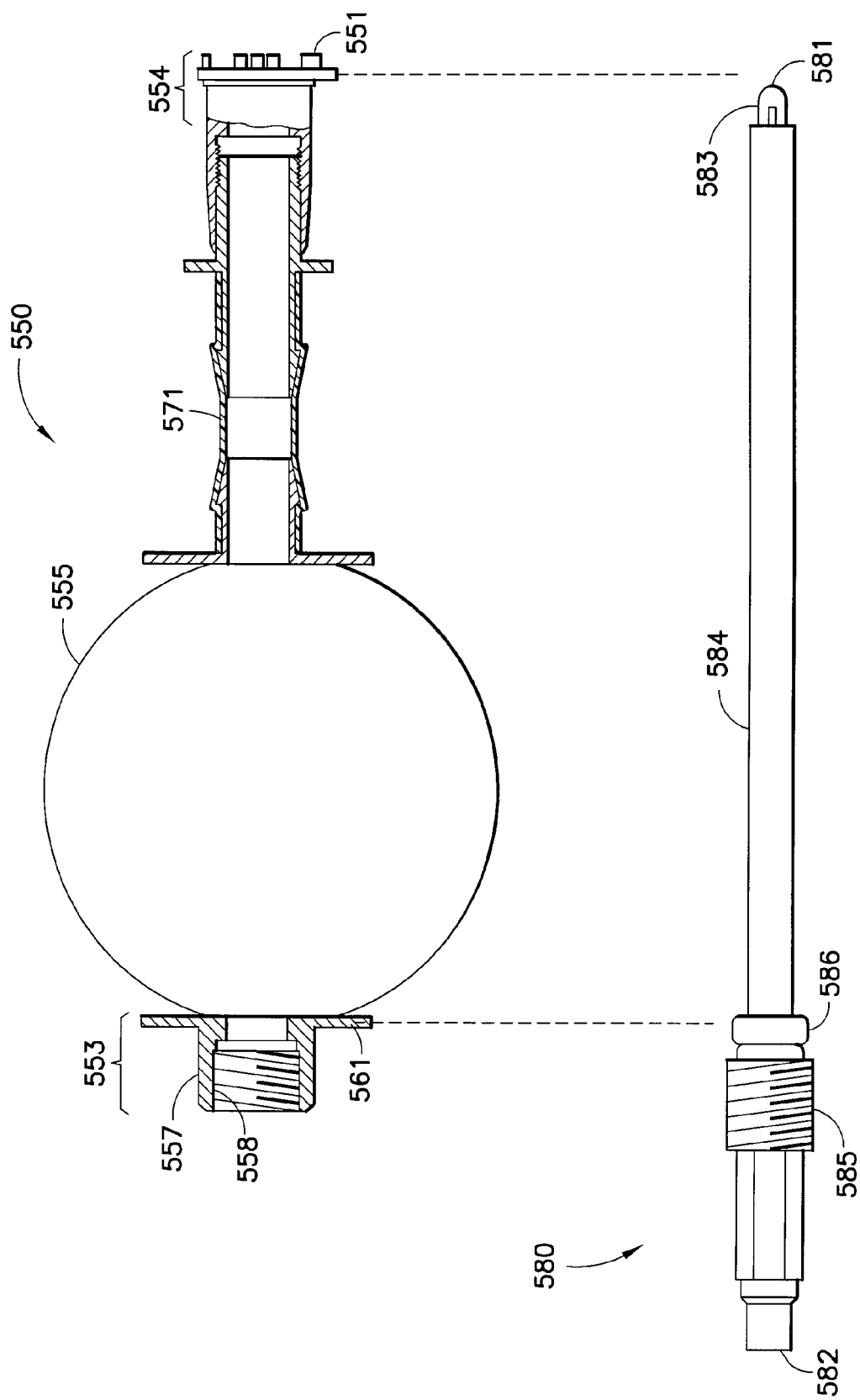
FIG. 7 is a side is a side cross-sectional view of the outer probe receiving element of FIGS. 6A-6B in the first expanded state, with a sensing probe disposed adjacent thereto to show desired relative dimensions (e.g., lengths) of the outer probe receiving element and the sensing probe.

FIG. 7 is a side is a side cross-sectional view of the outer probe receiving element 550 of FIGS. 6A-6B in the first expanded state, with a sensing probe 580 disposed adjacent thereto to show desired relative dimensions (e.g., lengths) of the outer probe receiving element 550 and the sensing probe 580. The probe 580 includes a first end 581 having a sensing portion 583 and a second end 582 proximate to a threaded portion 585 and optional sealing element 586, with a shaft 584 disposed between the two ends 581, 582. The outer threaded portion 585 of the probe 580 is engageable with the inner threaded portion 558 of the mounting element 553, and the sealing element 586 may engage the sealing surface 557. To ensure that the outer probe receiving element 580 remains sealed against contaminants, so as to allow sterilization of the outer probe receiving element 550 and probe 580 in combination, the insertable probe length should be less than or equal to an interior length of the outer probe receiving element 550. That is, the probe receiving element 550 is preferably adjustable to an interior length greater than the insertable probe length. When the probe 580 is mounted to the outer probe receiving element 550, and when the outer probe receiving element 550 is in an expanded (elongated) state (such as shown in FIG. 7), the tip 581 and sensing portion 583 of the sensing probe 580 should not protrude beyond the coupling 554 to permit sterilization of the combination prior to engagement between the outer probe receiving element 550 and the inner outer probe receiving element 510.

Figure 8:
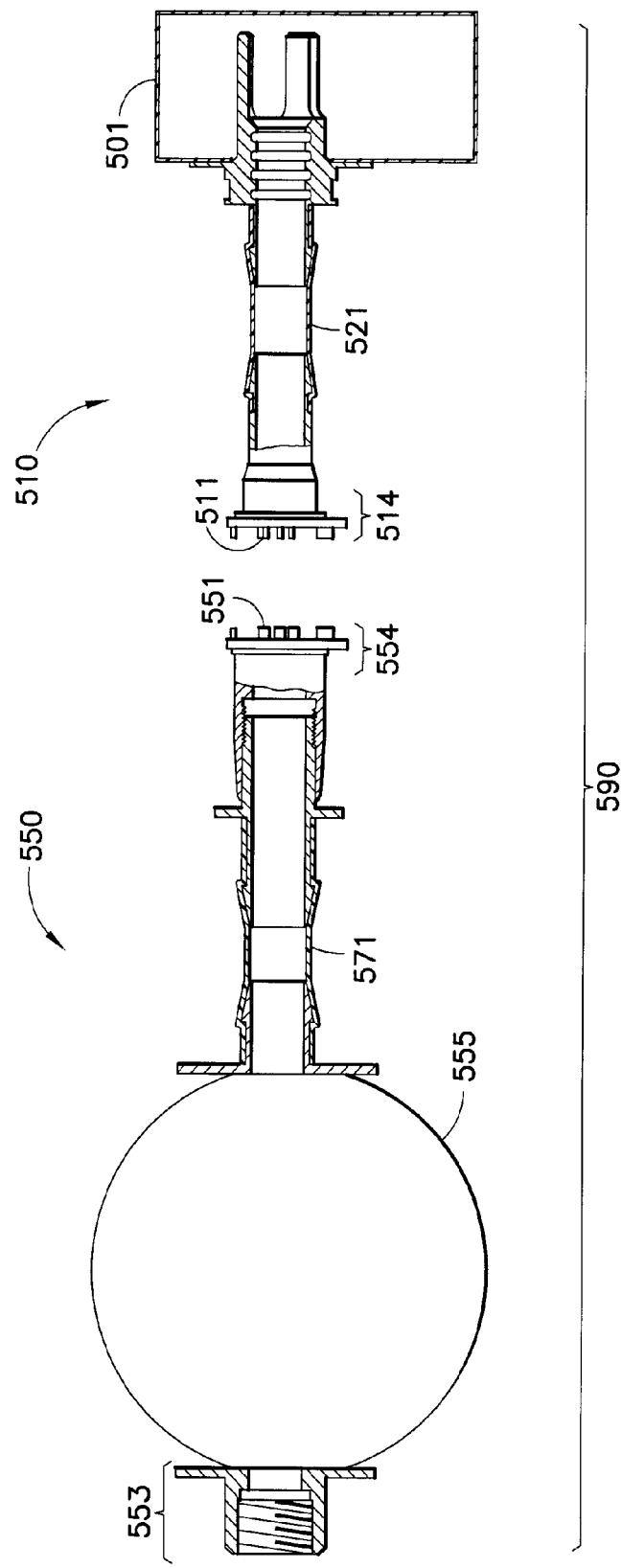
FIG. 8 is a side cross-sectional assembly view of the inner and outer probe receiving elements of FIGS. 5, 6A-6B, and 7, with the outer probe receiving element illustrated in an expanded state.

FIG. 8 is a side cross-sectional assembly view of the inner and outer probe receiving elements 510, 550 of FIGS. 5, 6A-6B, and 7, with the outer probe receiving element 550 illustrated in an expanded state, and with the inner probe receiving element 510 mated to a portion of a fluid processing apparatus 501. The combination of the two probe receiving elements 510, 550 constitutes a probe receiving assembly or system 590 adapted for sterile insertion of a portion of a probe (e.g., probe 580) into the interior of a fluid processing apparatus 501.

Figure 9:
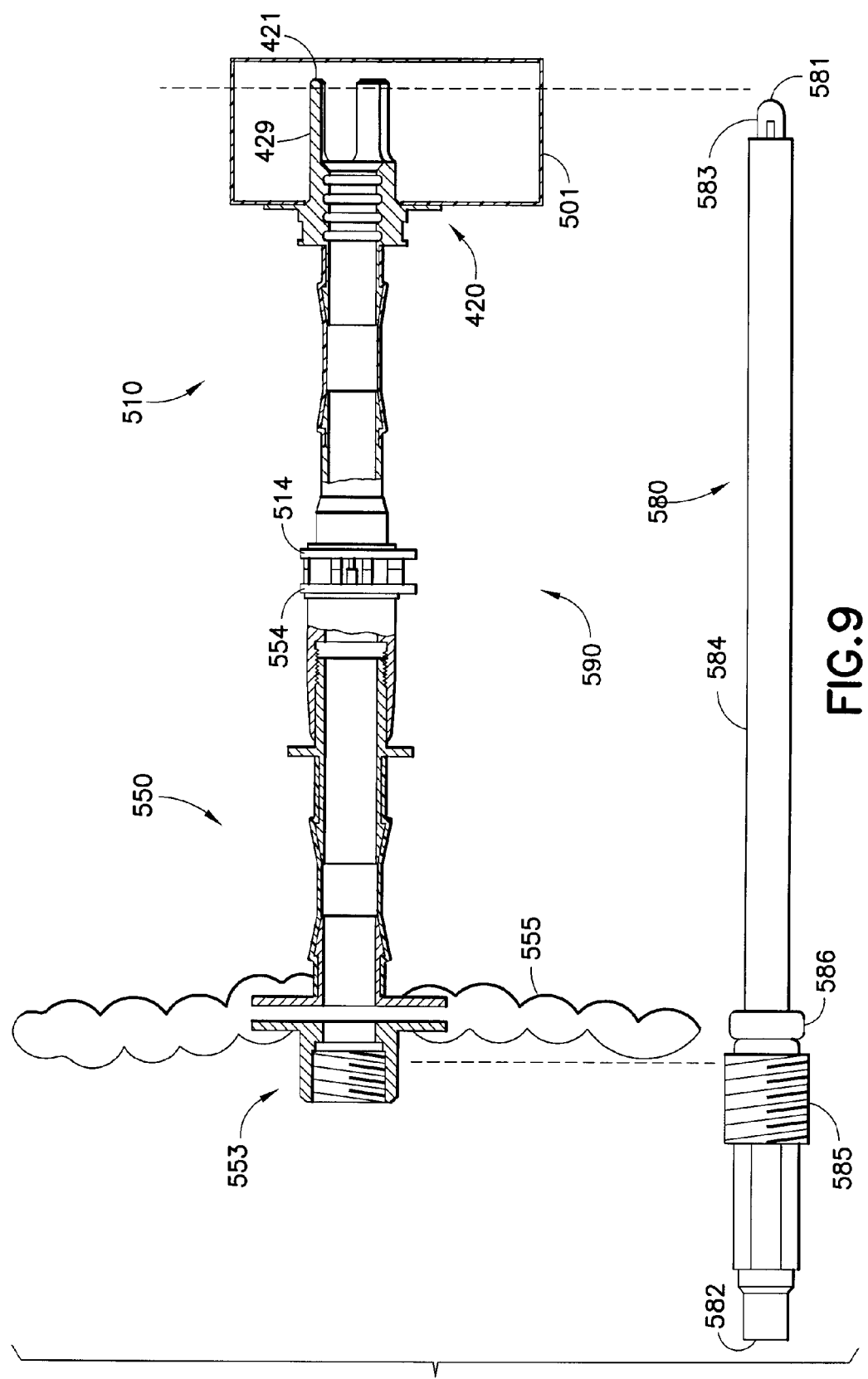
FIG. 9 is a side cross-sectional view of the inner and outer probe receiving elements of FIG. 8 engaged to one another, with the outer probe receiving element illustrated in a compressed state, and further providing a sensing probe disposed adjacent thereto to show desired relative dimensions (e.g., lengths) of the receiving elements in such state and the sensing probe.

FIG. 9 is a side cross-sectional view of the inner and outer probe receiving elements of FIG. 8 engaged to one another to form assembly or system 590, with the outer probe receiving element 550 illustrated in a compressed state, and further providing a sensing probe 580 disposed adjacent thereto to show desired relative dimensions (e.g., lengths) of the receiving elements 510, 550 in such state and the sensing probe 580. As shown in FIG. 9, the probe 580 preferably does not protrude beyond the protective surround 429 of the fitment 420 when such a protective surround is provided; however the insertion length of the probe 580 should be at least about as long as the combined interior length of the inner probe receiving element 510 and the interior length of the outer probe receiving element 550 in a compressed state, so as to position a sensing portion 583 of the probe 580 in or near the contents fluid processing tank 501.

Figure 10:
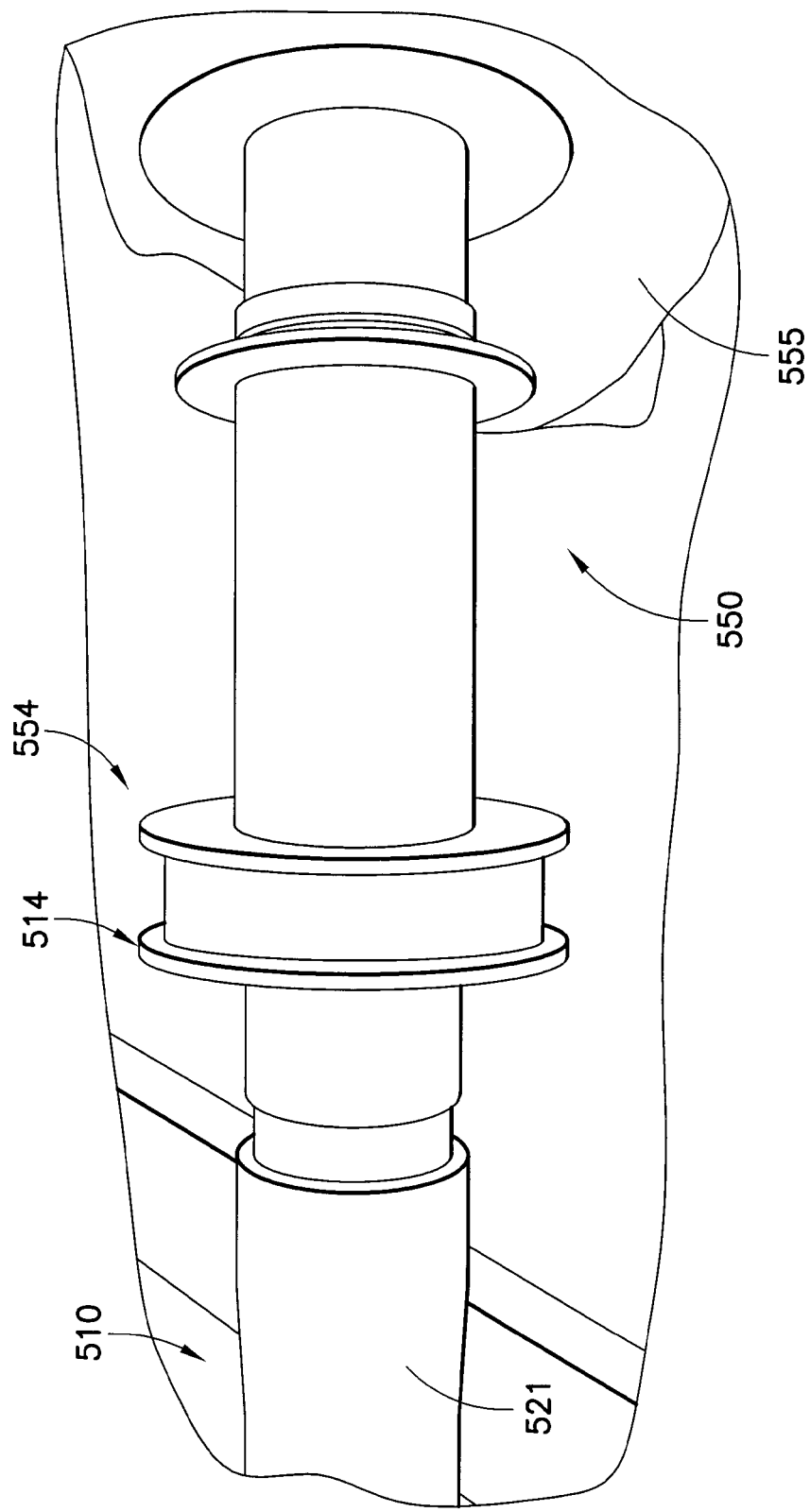
FIG. 10 is a photograph showing coupled portions of inner and outer receiving elements as previously described.

FIG. 10 is a photograph showing coupled portions of inner and outer receiving elements 510, 550 as previously described, with the coupling elements 514, 554 engaged to one another to make a sterile connection between a gas permeable contaminant barrier material 555 of the outer receiving element 550 and the inner receiving element 510 that includes a tube 521.

Figure 11:
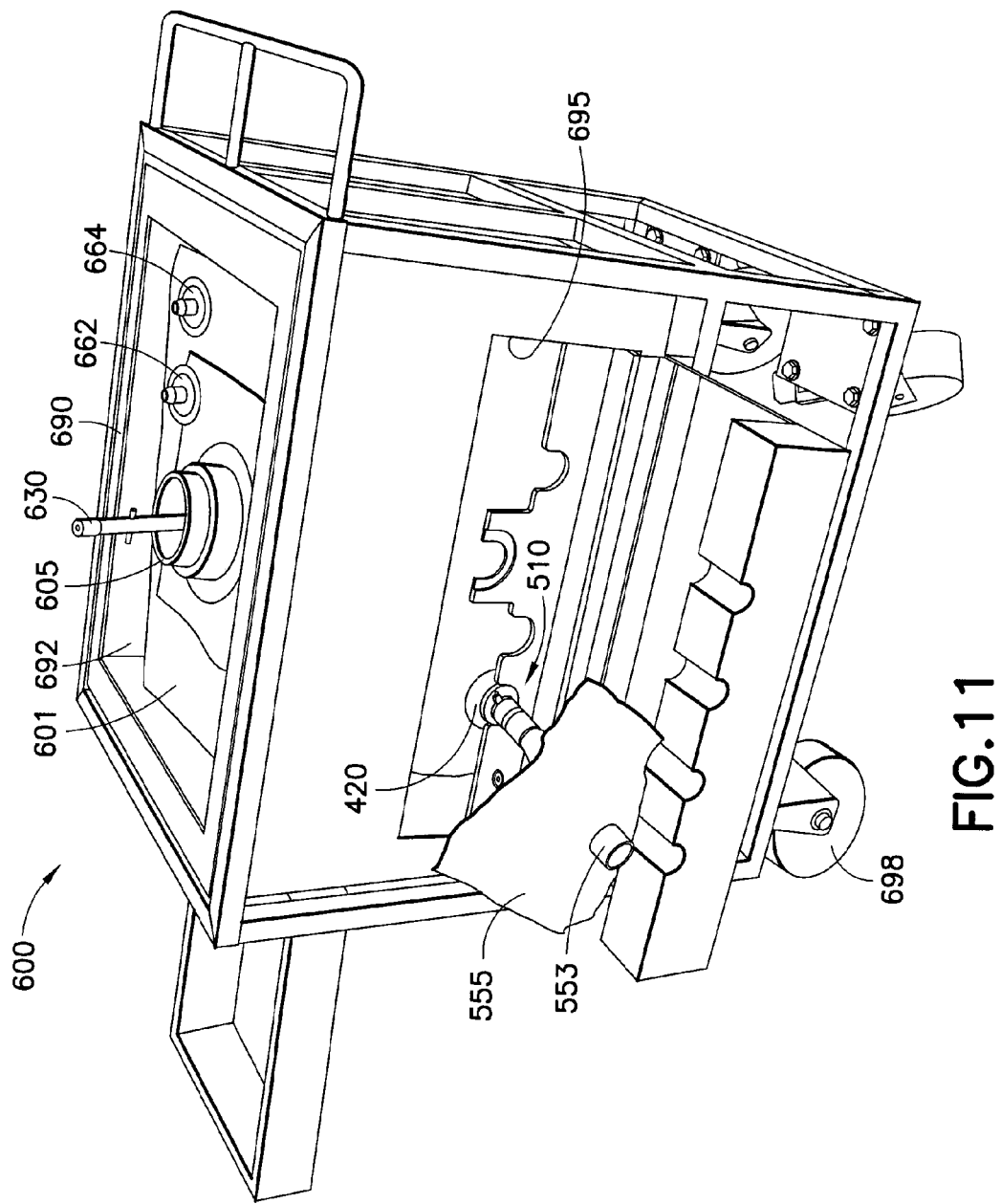
FIG. 11 is a side view photograph of a film-based fluid processing apparatus having a mixing paddle and suitable for use as a bioreactor, disposed within a cart-mounted support frame having side and top openings, with the fluid processing apparatus having coupled inner and outer receiving elements as previously described, and with the outer receiving element being in a compressed state.

FIG. 11 is a side view photograph of a film-based fluid processing apparatus 601 having a mixing paddle and suitable for use as a bioreactor 600, disposed within a cart-mounted support frame 690 having wheels 698, a side opening or window 695, and a top opening or window 692. The fluid processing apparatus 601 further includes a coupling guide 605 for mating the apparatus 601 with a support rod 630 adapted to drive a mixing paddle (not shown) preferably disposed within an integral sleeve (not shown) within the fluid processing apparatus 601 to mix the contents thereof. The fluid processing apparatus 601 further includes sealable ports 662, 664. Coupled along a side portion of the fluid processing apparatus 601 is a fitment 420 of an inner probe receiving element 510, mated to an outer probe receiving element having a gas permeable contaminant barrier material 555 (shown a compressed state) and a probe mounting element 553.

Figure 12:
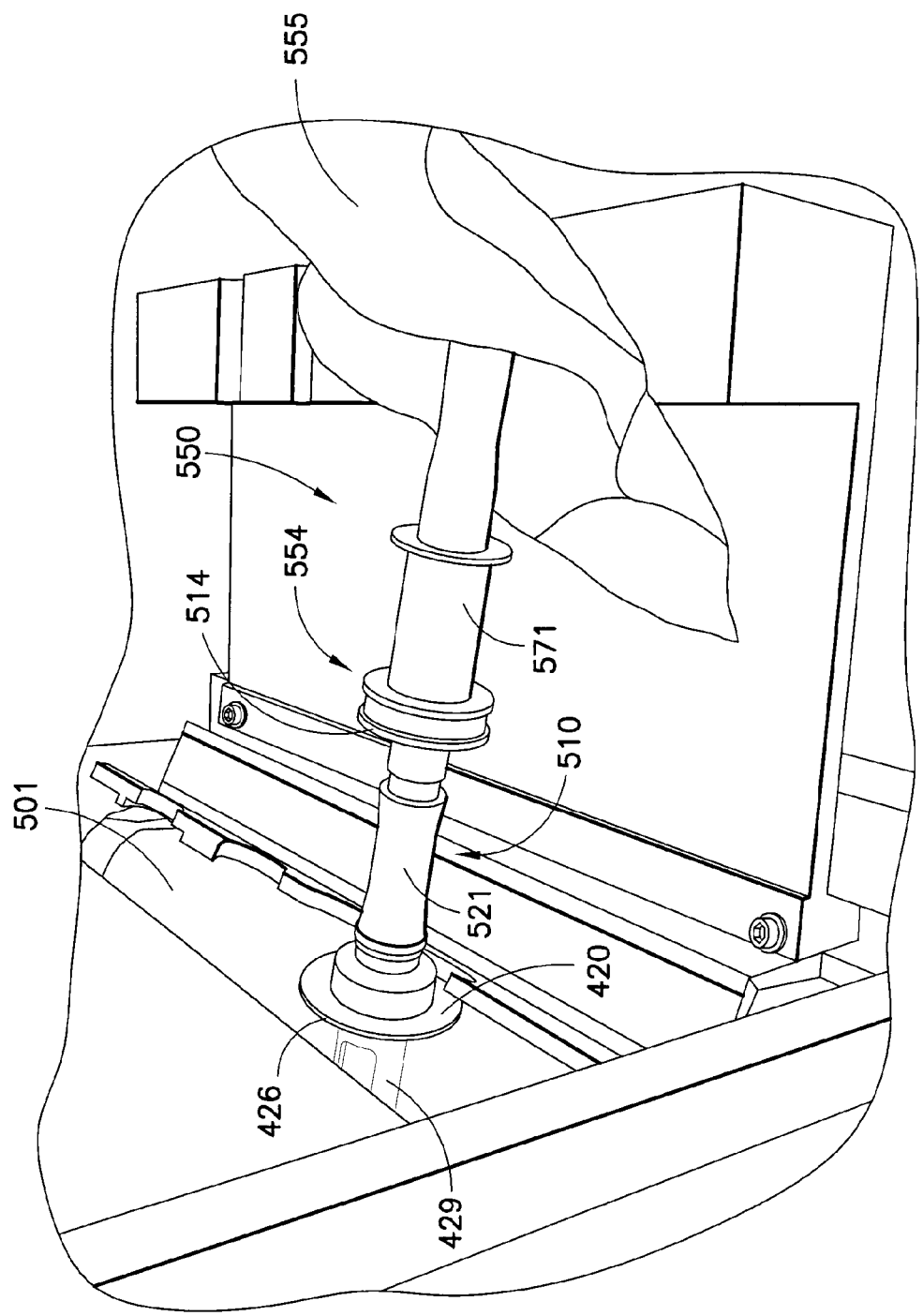
FIG. 12 is an end view photograph of the coupled receiving elements and fluid processing apparatus of FIG. 11.

FIG. 12 is an end view photograph of the coupled receiving elements 510, 550 and fluid processing apparatus 501 of FIG. 11. Disposed within the fluid processing apparatus 501 is the protective surround portion 429 of the fitment 420 of the inner receiving element 510, with the flange portion sealed to the fluid processing apparatus 501. A tube portion 521 of the inner receiving element 510 leads to an inner coupling 514 that is matably engaged in sterile fashion to an outer coupling 554 of the outer probe receiving element 550, having a tube portion 571 and a gas permeable contaminant barrier material 555.

Consistent with the description of various elements of a bioreactor probe connection system, various method steps may be employed to facilitate sterile connection of a sensor probe with a fluid processing apparatus according to one embodiment of the present invention. A first method step includes inserting an elongated probe into a first probe receiving element having (a) a mounting element adapted to engage a portion of said probe; (b) a gas-permeable contaminant barrier material bounding an interior volume including a first passage permitting insertion of at least a portion of said probe therethrough; and (c) a first coupling. A second method step includes supplying a sterilant gas or vapor through the gas-permeable contaminant barrier material into an interior volume of said first probe receiving element to sterilize said probe, following said probe insertion step. A third step includes matably engaging the first probe receiving element to a second probe receiving element securable to said fluid processing apparatus, the second probe receiving element defining a second passage, wherein said engagement is between a second coupling of said second probe receiving element and the first coupling. A fourth step includes inserting a portion of the probe through the engaged first and second coupling to a position in fluid communication with an interior portion of said fluid processing apparatus. Optional further steps include: monitoring a condition within said fluid processing apparatus utilizing the probe; collapsing at least a portion of said gas-permeable contaminant barrier material during said insertion of the probe through the engaged first and second couplings; and utilizing said probe in a performing a bioreaction process.

While the invention has been described herein in reference to specific aspects, features and illustrative embodiments of the invention, it will be appreciated that the utility of the invention is not thus limited, but rather extends to and encompasses numerous other variations, modifications and alternative embodiments, as will suggest themselves to those of ordinary skill in the field of the present invention, based on the disclosure herein. Correspondingly, the invention as hereinafter claimed is intended to be broadly construed and interpreted, as including all such variations, modifications and alternative embodiments, within its spirit and scope.

What is claimed is:

1. A first probe receiving element adapted to permit sterile connection of a probe with a fluid processing apparatus having associated therewith a second coupling adapted to permit insertion of at least a portion of said probe therethrough, the first probe receiving element comprising:
   a mounting element adapted to engage a portion of said probe;
   a tubular portion including an inner wall surface bounding an interior volume including a first passage permitting insertion of at least a portion of said probe;
   a collapsible section or collapsible bag comprising a gas permeable contaminant barrier material arranged to admit a sterilant gas or vapor into the interior volume and into contact with the inner wall surface bounding the interior volume;
   a first coupling comprising a first removable membrane or barrier; and
   a second coupling comprising a second removable membrane or barrier;
   wherein each of the first removable membrane or barrier and the second removable membrane or barrier is arranged to be removed following mating of the first coupling and the second coupling; and
   wherein following engagement between the first coupling and the second coupling, the first probe receiving element is adapted to receive at least a portion of said probe through the engaged first and second couplings to a position in fluid communication with an interior portion of said fluid processing apparatus.

2. The first probe receiving element of claim 1, wherein the collapsible section or collapsible bag has an adjustable length.

3. The first probe receiving element of claim 1, further comprising said probe, wherein said probe is adapted to generate an output signal indicative of any of temperature, pressure, pH, oxygen concentration, chemical presence, and chemical concentration.

4. The first probe receiving element of claim 1, being coupled with the fluid processing apparatus including an interior portion adapted to contain a fluid, wherein the collapsible section or collapsible bag comprising the gas permeable contaminant barrier material is arranged external to the interior portion of said fluid processing apparatus.

5. A system adapted for sterile connection of a probe with a fluid processing apparatus, the system comprising:
   a first probe receiving element according to claim 1; and
   a second probe receiving element securable to said fluid processing apparatus and securable to the first probe receiving element, the second probe receiving element comprising the second coupling and defining a second passage, wherein following engagement between the first coupling and the second coupling, the system is adapted to receive at least a portion of said probe through the engaged first and second couplings, and through the second passage, to a position in fluid communication with an interior portion of said fluid processing apparatus.

6. The system of claim 5, wherein the first probe receiving element has an adjustable interior length.

7. The system of claim 6, wherein said probe is engageable to the mounting element to define an insertable probe length, and the first probe receiving element is adjustable to an interior length greater than the insertable probe length.

8. The system of claim 5, wherein the second probe receiving element is welded to the fluid processing apparatus.

9. The system of claim 5, wherein the second probe receiving element comprises a plurality of sealing elements adapted to engage a portion of said probe.

10. The system of claim 5, wherein the second probe receiving element comprises a removable or rupturable membrane adapted to temporarily seal an interior space of said second probe receiving element.

11. The system of claim 5, wherein the second probe receiving element comprises a protective surround in fluid communication with an interior portion of the fluid processing apparatus and that permits contents of the fluid processing apparatus to circulate across at least a portion of the probe.

12. The system of claim 5, further comprising said probe, wherein said probe is adapted to generate an output signal indicative of any of temperature, pressure, pH, oxygen concentration, chemical presence, and chemical concentration.

13. A bioreactor comprising the system of claim 5.

14. A method to permit sterile connection of a probe with a fluid processing apparatus, the method comprising:

inserting an elongated probe into a first probe receiving element according to claim 1;

following said probe insertion, supplying a sterilant gas or vapor through the gas-permeable contaminant barrier material into the interior volume of said first probe receiving element to sterilize said probe;

engaging the first probe receiving element to a second probe receiving element securable to said fluid processing apparatus, the second probe receiving element defining a second passage, wherein said engagement is between a second coupling of said second probe receiving element and the first coupling; and inserting a portion of the probe through the engaged first and second couplings to a position in fluid communication with an interior portion of said fluid processing apparatus.

15. The method of claim 14, further comprising making a sterile connection between the first coupling and the second coupling in a non-sterile environment.

16. The method of claim 14, further comprising monitoring a condition within said fluid processing apparatus utilizing the probe.

17. The method of claim 14, further comprising utilizing said probe in performing a bioreaction process.

18. The method of claim 14, wherein said supplying of sterilant gas or vapor through the gas-permeable contaminant barrier is performed when the collapsible section or collapsible bag is in an expanded state.

* * * * *